United States Patent [19]

Boggs et al.

[11] Patent Number: 4,946,964
[45] Date of Patent: Aug. 7, 1990

[54] PHOTOGRAPHIC COMPOUNDS

[75] Inventors: Roger A. Boggs, Wayland; John B. Mahoney, Tewksbury; Avinash C. Mehta, Belmont; William C. Schwarzel, Billerica; Lloyd D. Taylor, Lexington, all of Mass.

[73] Assignee: Polaroid Corporation, Cambridge, Mass.

[21] Appl. No.: 131,911

[22] Filed: Dec. 11, 1987

Related U.S. Application Data

[62] Division of Ser. No. 846,584, Mar. 31, 1986, Pat. No. 4,743,533.

[51] Int. Cl.$^5$ .......................................... C07D 257/04
[52] U.S. Cl. ...................................................... 548/251
[58] Field of Search ......................................... 548/251

[56] References Cited

U.S. PATENT DOCUMENTS

| | | | |
|---|---|---|---|
| 3,260,597 | 7/1966 | Weyerts et al. | 96/3 |
| 3,265,498 | 8/1966 | Rogers et al. | 96/3 |
| 3,698,898 | 10/1972 | Grasshoff et al. | 96/3 |
| 3,938,996 | 2/1976 | Fujiwhara et al. | 96/66.3 |
| 4,009,029 | 2/1977 | Hammond et al. | 96/3 |
| 4,049,455 | 10/1977 | Kikuchi et al. | 548/251 X |
| 4,355,092 | 10/1982 | Mehta et al. | 430/219 |

FOREIGN PATENT DOCUMENTS 2427183 12/1974 Fed. Rep. of Germany .

*Primary Examiner*—David B. Springer
*Attorney, Agent, or Firm*—Gaetano D. Maccarone

[57] ABSTRACT

There is described a photographic system wherein development of an exposed photosensitive element with an aqueous alkaline photographic developing composition is effected in the presence of a compound represented by the formula

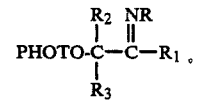

wherein R is $-OH$, $-OR_4$, $-NH_2-NHR_5$ or $-NR_4R_6$; $R_1$ is hydrogen, $-NH_2$, alkyl, substituted alkyl, aryl or substituted aryl; $R_2$ and $R_3$ each independently is hydrogen, alkyl, aralkyl or aryl; $R_4$ is a protecting group which can be removed in the presence of a base; $R_5$ is an activating group which can render the neighboring hydrogen atom acidic; $R_6$ is an electron withdrawing group which is capable of stabilizing the negative charge on the nitrogen atom which is produced upon removal of $R_4$ upon contact with alkali; and PHOTO is a photographically useful group.

The compounds provide controlled release of the photographically useful group by a base-catalyzed elimination when contacted by the aqueous alkaline processing composition.

6 Claims, No Drawings

PHOTOGRAPHIC COMPOUNDS

This is a division of application Ser. No. 846,584, filed Mar. 31, 1986 now U.S. Pat. No. 4,743,533.

BACKGROUND OF THE INVENTION

The application relates to a photographic system, including photographic products and processes, which utilize compounds capable of releasing a photographically useful material when contacted with an aqueous alkaline processing composition.

In various photographic systems for forming images, whether in black and white or in color, it is often desirable to include in the photographic film unit one or more of the various photographic reagents required for development and/or to enhance image quality. This practice extends to both conventional systems for forming negative images and also to various systems such as diffusion transfer wherein a positive image in silver or in color is obtained. In many instances the photographic reagent may be contained initially in either the processing composition applied for development and image formation or in the film unit itself. The latter embodiment is typically preferred so as to reduce the number of ingredients required in the processing composition. In other instances the particular photographic reagent is not sufficiently stable in alkali to provide the requisite shelf life for the processing composition or the reagent is not compatible and/or reacts with another reagent in the processing composition and therefore must be contained initially in the film unit. In still other instances the reagent must be provided at some particular time in the development process which requires that it be present in a specified layer or in specified proximity to another layer in the film unit.

In all the foregoing instances it is desirable that the reagent be contained in the desired layer or layers in a form that is stable and non-migratory or nondiffusible and yet available when required at a particular time in the development process. To accomplish this result it is known in the art to attach a blocking moiety which prevents the reagent from reacting with the other photographic materials present in the film unit or migrating or diffusing prior to the time when photographic development is effected but which will release the photographic reagent at the desired time such as by reaction with the aqueous alkaline processing composition.

It is known in the art to utilize development restrainers and development restrainer precursors in photographic applications. A predetermined level of development usually will take place before the development restrainers or development restrainer precursors function to inhibit or control further development. The blocked development restrainers are designed to provide a controlled release of the development restrainer during the development process. Such blocked development restrainers are disclosed, for example, in U.S. Pat. Nos. 3,260,597 and 3,265,498 which disclose hydrolyzable blocked restrainers; U.S. Pat. No. 3,698,898 which discloses the use of guinone—or naphthoquinonemethide precursors which release a photographic reagent such as 1-phenyl-5-mercaptotetrazole in the presence of alkali; U.S. Pat. No. 3,938,996 which discloses the use of a carbocylic blocking group which includes an oxime group (e.g. —C=N—OH); U.S. Pat. No. 4,009,029 which discloses a class of cyanoethyl—containing blocked development restrainers; and German Offenlegungsschrift No. 2,427,813 which discloses various blocked development restrainers.

SUMMARY OF THE INVENTION

It is an object of this invention to provide a novel photographic system.

It is another object of the invention to provide a photographic system which utilizes a compound capable of providing controlled release of a photographically useful group when contacted by an aqueous alkaline processing composition.

It is still another object of the invention to provide a system which utilizes a compound capable of providing controlled release of a photographically useful group during the development process.

A further object is to provide a system which utilizes a compound capable of providing controlled release of a development restrainer during the development process.

Still another object to provide novel photographic products and processes.

Yet another object is to provide novel compounds.

BRIEF SUMMARY OF THE INVENTION

These and other objects and advantages are accomplished in accordance with the invention by providing a photographic system wherein development of an exposed photosensitive element is carried out in the presence of a compound represented by the formula

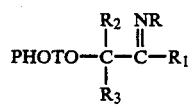  FORMULA A wherein

R is —OH, —OR$_4$, —NH$_2$ —NHR$_5$ or —NR$_4$R$_6$; R$_1$ is hydrogen —NH$_2$, alkyl, preferably having from 1 to 6 carbon atoms, substituted alkyl, aryl such as phenyl or naphthyl, or substituted aryl; R$_2$ and R$_3$ each independently is hydrogen, alkyl, preferably having from 1 to 6 carbon atoms, aralkyl such as benzyl or aryl such as phenyl;

R$_4$ is a protective group which is removable in the presence of a base;

R$_5$ is an activating group which will render the neighboring hydrogen atom acidic; R$_6$ is an electron withdrawing group which is capable of stabilizing the negative charge on the nitrogen atom which is produced upon removal of R$_4$ upon contact with alkali; and PHOTO represents a photographically useful group such as a photographic reagent residue or a photographically acceptable addition salt thereof, or a dye.

The nature of the protecting group R$_4$ can vary provided that the group will be removed upon contact with base. Suitable blocking groups include —CONHR$_7$, —COR$_7$, —COOR$_7$ and —SO$_2$R$_7$, wherein R$_7$ is alkyl, preferably having from 1 to 6 carbon atoms, aryl such as phenyl or naphthyl, alkaryl such as tolyl, aralkyl such as benzyl, or a carbocyclic radical such as cyclohexyl.

The nature of the activating group R$_5$ can vary provided that the group is capable of rendering a neighboring hydrogen atom acidic. Suitable blocking groups include —COR$_7$, —COOR$_7$ and —SO$_2$R$_7$ where R$_7$ is as previously defined.

The nature of the electron withdrawing group R$_6$ can vary provide that the group is capable of stabilizing the negative charge on the nitrogen atom which is produced upon removal of $R_4$ upon contact with alkali. Typical suitable electron withdrawing groups include —$COR_7$, —$COOR_7$ and —$SO_2R_7$, where $R_7$ is as previosuly defined.

PHOTO may be any photographically useful group such as the residue of any of many photographic reagents such as development restrainers, e.g., mercaptoazoles; silver halide solvents, e.g., sodium and potassium thiocyanates; antifoggants; and organic silver halide developing agents, e.g., those of the dihydroxybenzene or aminophenol series. Many of each of these types of photographic reagents are well known to those skilled in the art and therefore extensive discussion of specific suitable reagents is not required here. PHOTO may also be the residue of a dye, e.g., an image dye, a filter dye, etc.

In a preferred embodiment of the invention $R_1$ is

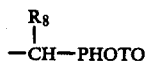

wherein $R_8$ is the same as $R_2$ and $R_3$ is hydrogen. These compounds according to the invention can be represented by the formula

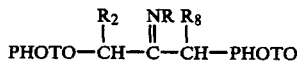 FORMULA B wherein $R_2$ and $R_8$ are the same and may be any of the groups defined above with respect to $R_2$. The compounds within Formula B possess only one isomeric form because of their symmetrical structure which is beneficial from the point of view of kinetic release.

It has been found that the compounds within Formula A which have one PHOTO group exist in the syn-(zusammen) and anti-(entgegen) isomeric forms and that there are significant kinetic differences in the photographic performance of the isomers. In general, the anti isomer is much faster releasing than the syn isomer. Because of the symmetrical structure of the compounds within Formula B there is always a PHOTO group moiety anti to the hydroxy group of the oxime function or the nitrogen atom of the tosyl hydrazone function and therefore the release of the PHOTO moiety from these compounds is more efficient. Thus, the PHOTO moiety which has anti-conformation with respect to the hydroxy group of the oxime function or the nitrogen atom of the tosyl hydrazone function will be released in the time period typically required for that moiety to perform its function in the photographic process. The other PHOTO moiety which is syn to the hydroxy group of the oxime function or the nitrogen atom of the tosyl hydrazone function is typically not released within the time period for photographic development.

The compounds within Formulas A and B provide a controlled release of the photographically useful group in the presence of alkali. The blocking group provides a timed releases of the PHOTO moiety in the alkaline environment typically encountered in the processing of photographic elements and particularly where the alkaline medium has a relatively high pH, e.g., in the range of from about 12 to about 14.

The rate of release of the PHOTO moiety is dependent upon a number of factors. As described above, the release rate varies significantly for the syn and anti isomeric forms of compounds which have one PHOTO group. The release rate is also dependent upon the hydroxyl ion concentration of the alkaline medium. The release of the PHOTO moiety requires ionization of the R group attached to the nitrogen atom and the amount of ionization that occurs is a function of the alkali concentration and the pKa of R. Accordingly, the pH-rate profile is sigmoidal pH(9-14) with a dependency on the PKa of R. The rate of release is dependent upon the hydroxyl concentration provided the pH is at or below the PKa of R. Significantly above the pKa of R, the rate of release is constant. The rate of release is also temperature dependent, that is, the rate increases as the temperature at which processing of the film unit is effected increases. Thus, where PHOTO is a photographic reagent residue for example, the compounds which are utilized according to the invention can provide more uniform sensitometry for the film units of the invention over a wide temperature range of processing. In other words, the sensitometry of such film units can be less temperature dependent than would otherwise be the case.

In a preferred embodiment of the invention the compounds within Formulas A and B are utilized to release a development restrainer during development of an exposed photosensitive element. In a particularly preferred embodiment where PHOTO is a development restrainer residue, PHOTO can be represented as

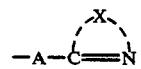 FORMULA C or

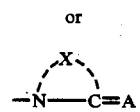 FORMULA D wherein A is sulfur or selenium and X represents the nonmetallic atoms necessary to form a nucleus which completes a five or six member heterocyclic moiety including substituted rings and fused rings. These compounds cleave in alkaline compositions to provide mercapto- or selenoazoles which are diffusible in aqueous alkaline photographic processing compositions. As stated previously the heterocyclic moiety includes substituted rings and fused rings. Where the heterocyclic moiety is substituted the substituent(s) may be attached to either a nitrogen atom or a carbon atom of the azole moiety. The preferred heterocyclic rings within Formulas C and D include groups wherein the heterocyclic atoms, i.e., atoms other than carbon, are members of a single heterocyclic ring rather than fused or condensed heterocyclic rings wherein the heterocyclic atoms are members of more than one heterocyclic ring. The development restrainer moieties within Formulas C and D include monoazoles such as benzoxazoles and benzothiazoles; imidazoles such as benzimidazoles; triazoles such as 1,2,4-triazoles and benzotriazoles; tetrazoles and pyrimidines. The most preferred heterocyclic moieties are tetrazoles and a particularly preferred heterocyclic moiety is a tetrazole substituted with a phenyl group which may itself be substituted as will be described more in detail below. Upon cleavage of the molecule which occurs between a PHOTO moiety and the adjacent carbon atom, the heterocyclic moiety, together with the sulfur or selenium atom, provides a development restrainer residue. When incorporated into a photographic element these compounds permit initial development to occur normally during processing of the element with an aqueous alkaline processing composition and then undergo cleavage to restrain or control further development.

In a preferred group of compounds which are utilized according to the invention, PHOTO is represented by the formulas

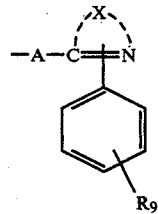

FORMULA E or

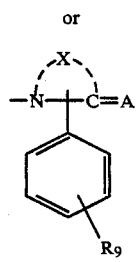

FORMULA F wherein $R_9$ is either a group which has a pKa of from about 7 to about 14, preferably at least about 8.5 or higher, which is ionizable to an anion wherein the silver salt of the moiety resulting from cleavage of the blocking group is more soluble in the pH range within which $R_9$ is ionized to an anion than it is below that pH range, or a precursor of such a group. Typical substituents which are suitable as $R_9$ include —OH, —COCH$_3$, —OCOCH$_3$, SO$_2$NH$_2$, —SO$_2$NHCH$_3$, —SO$_2$NHC$_8$H$_{17}$,

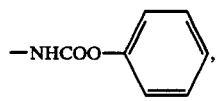

—NHCOOCH$_3$, —NHSO$_2$CH$_3$,

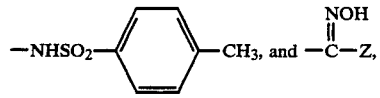

where Z is hydrogen, alkyl having from 1 to 10 carbon atoms, phenyl, substituted phenyl or aralkyl such as benzyl or phenethyl.

As stated above, $R_9$ may also be a precursor of a substituent having the requisite properties and the desired substituent may be formed in situ. For example, it is possible to incorporate in the film unit as a precursor a compound having an azole moiety within Formulas E and F which has a hydrolyzable ester group on the phenyl ring and generate the desired hydroxy group in situ during photographic processing. It should also be noted here that the acetyl group which can be substituted on the phenyl ring does not ionize to any appreciable extent to form an anion in an aqueous alkaline processing composition. However, the presence in a film unit of a compound having an azole moiety within Formulas E and F having an acetyl group substituted on the phenyl ring can provide advantageous results. It would appear that the compound would undergo a change in the aqueous alkaline processing composition and that the acetyl group is a precursor of a group which has the requisite properties described above.

It has been found that the Arrhenius activation energy (Ea) necessary to cause these preferred compounds to undergo release of the PHOTO moiety is advantageously high, i.e., in the range of from about 20 to about 25 kcal/mole. The rate at which the release reaction increases with temperature is a function of the activation energy. For example, for an increase in temperature from 20° C. to 30° C., it hs been calculated that the reaction rate will increase by a factor of 2 when Ea is 12.2, by a factor of about 3 when Ea is 19.3, by a factor of about 4 when Ea is 24.4 and by a factor of about 5 when Ea is 28.3. Further, it has also been found that these preferred compounds have a high activation energy independent of their release rate at room temperature and that the room temperature release rates of the respective compounds vary over a considerable range. Typically, for such release reactions with other compounds, when the room temperature release rate is relatively fast, the activation energy tends to be about 10. Accordingly, it is possible to select, according to the invention, for a particular photographic system a compound which has a desired release rate at room temperature, a much slower release rate at lower temperatures and a much higher release rate at higher temperatures.

As discussed previously the rate of release of the PHOTO moiety from the compounds of the invention is dependent upon factors such as temperature, the hydroxyl ion concentration relative to the pKa of the R group and the conformation of the R group with respect to the PHOTO moiety. In addition the compounds wherein PHOTO is a moiety within Formulas C-F release the PHOTO moiety at varying rates dependent upon where it is attached to the other part of of the molecule, i.e., whether it is attached through the sulfur or selenium on the one hand or through a nitrogen atom on the other. Such variables provide further latitude in the selection of a compound having release rates desired for a particular application.

DESCRIPTION OF THE PREFERRED EMBODIMENTS

Preferred compounds according to the invention include those represented by the formulas

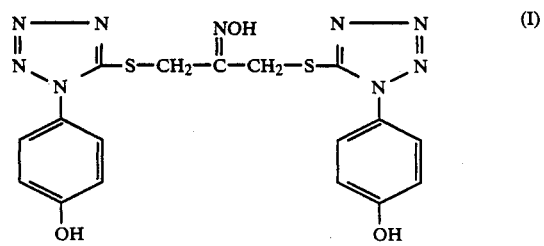

(I)

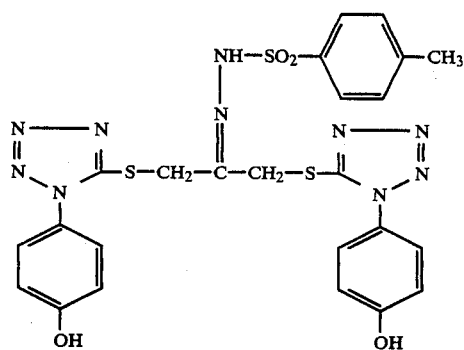 (II)

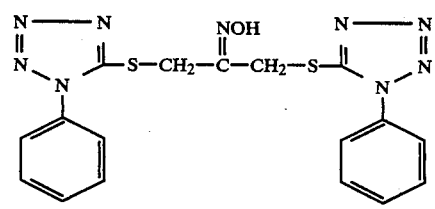 (III)

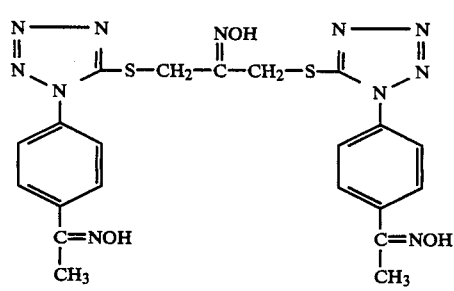 (IV)

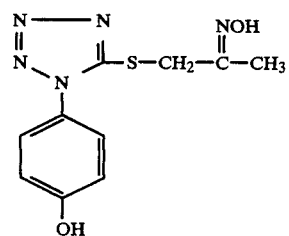 (V)

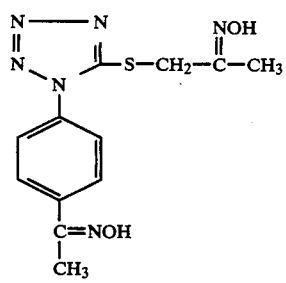 (VI)

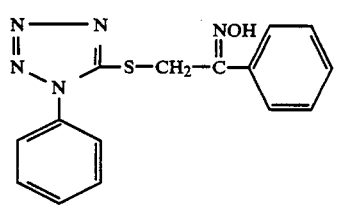 (VII)

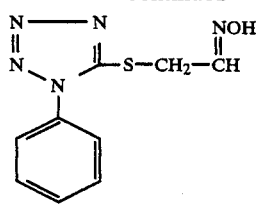 (VIII)

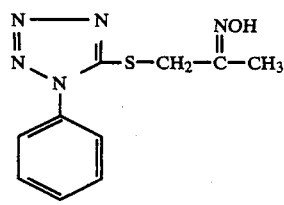 (IX)

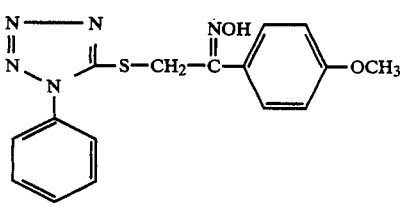 (X)

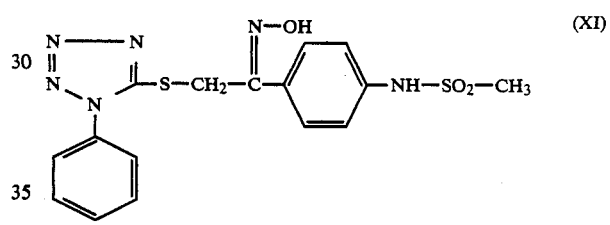 (XI)

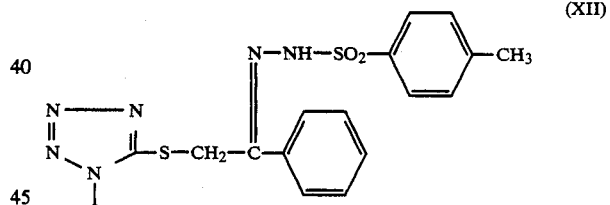 (XII)

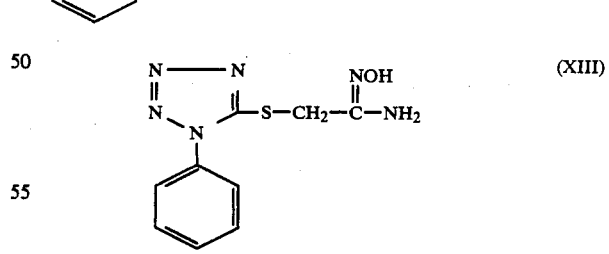 (XIII)

The release kinetics of the compounds of the invention vary over a wide range. The t½ times in solution, i.e., the time required for one-half of the material to undergo cleavage with release of the PHOTO moiety, for some of the compounds illustrated above are shown in Table I. The values were obtained using $1 \times 10^{-4}$ molar concentrations in 30% acetonitrile/0.25N aqueous potassium hydroxide solution at a temperature of $22° \pm 0.1°$ C.

TABLE I

| COMPOUND | $t_{\frac{1}{2}}$ (seconds) |
|---|---|
| I | 51.1 |
| III | 8.9 |
| V | 40.5 |
| VI | 28.9 |
| VII | 4–6 |
| VIII | 49.1 |
|  | 1020.0* |
| IX | 22.5 |
| X | 4.3 |
| XI | 7.6 |
| XII | 165.0 |
| XIII | 546.0 |

*syn isomer

The Arrhenius activation energies (Ea) for compounds I, IX and X were found to be 21.8 kcal/mole, 26.5 kcal/mole and 21.9 kcal/mole, respectively. The Arrhenius activation energy (Ea) was calculated by plotting the log of the observed rate constant vs 1/T (° K.) for each compound.

The compounds of the invention may be prepared by various synthetic reaction sequences which are within the skill of those in the art. According to one such method the compound from which the photographically useful group is derived, for example, 1-(4-hydroxyphenyl)-1H-tetrazole-5-thiol, can be reacted with an α, α'-dihaloketone in a solution of an organic solvent such a acetone in the presence of the suitable base such as sodium bicarbonate, sodium hydroxide or potassium hydroxide to provide an intermediate which can then be oximated using known methods such as reacting with hydroxylamine hydrochloride in a suitable solvent or mixture of solvents in the presence of a base such as sodium bicarbonate, sodium acetate, sodium hydroxide or sodium carbonate at temperatures ranging from ambient to refluxing temperature of the solvent to give the desired symmetrical bis compound. In a similar fashion the intermediate can be reacted with sulfonyl hydrazides to obtain the desired tosyl hydrazones. Following the same methodology the α, α'-dihaloketones can be utilized to derivatize other photographically useful groups and the intermediates thus obtained can be converted to the oximes or tosyl hydrazones to provide the desired final products.

The starting materials are commercially available in many cases and generally can be made by reactions which are known to those skilled in the art. For example, 2-mercaptoimidazoles can be prepared by the reactions disclosed in the Chemistry of Heterocyclic Compounds Vol. 6: Imidazole and Its Derivatives, Part I, Hoffman Interscience Publishers, Inc., New York, 1953, pages 77–85; hydroxyalkylimidazoles, ibid, pages 99–104; chloroalkylimidazoles, ibid, page 121; mercaptothiazoles and mercaptobenzothiazoles can be prepared according to the methods disclosed in The Chemistry of Heterocyclic Compounds Vol. 34: Thiazole and Its Derivatives, Part I, Metzger, John Wiley and Sons, 1979, pages 260–269; Part 2, pages 370–377; benzoxazolethiones can be prepared according to the methods disclosed in Heterocyclic Compounds, Vol. 5, Elderfield, John Wiley and Sons, 1957, pages 439–444; 5-mercapto-1,3,4-oxadiazoles can be prepared according to the methods disclosed in Heterocyclic Compounds, Vol. 7, Elderfield, John Wiley and Sons, 1961, page 352; mercapto-1,3,4 thiadiazoles, ibid, pages 587–612; and tetrazoles by the techniques disclosed in Heterocyclic Compounds, Vol. 8, Elderfield, John Wiley and Sons, 1967, pages 1–107. Mercapto-1,2,4-triazoles can be prepared by known literature techniques as described, for example, in J. Chem. Soc. E. Hoggarth 1163 (1949). The selenazoles may be prepared by similar techniques.

The compounds of the invention may be present in photographic elements in any appropriate location and in any amount which is required to accomplish their intended purpose. The amount necessary in any particular instance is dependent upon a number of factors such as, for example, the compound utilized, the type of photographic element, the location of the compound in the photographic element and the result desired. Routine scoping tests may be used to ascertain the concentration appropriate for any given photographic element. In a preferred embodiment of the invention the compounds are incorporated in diffusion transfer photographic film units as will be discussed in more detail below herein. In such film units the compounds may be incorporated in the photosensitive element and/or the image-receiving element or in a cover sheet.

The compounds of the invention may be utilized in any photographic system wherein the release of a photographically useful group during development of an exposed photosensitive element is desired, including photographic systems for forming images in black and white or in color and those wherein the final image is a silver image or one formed by other image-forming materials. Further, where appropriate, the compounds may be utilized in various layers of a multilayer photographic system in varying concentrations to ensure the desired distribution of the photographically useful group during processing.

The advantageous results which can be obtained through the use of a preferred species of the compounds according to the invention, i.e., those wherein the PHOTO moiety is an azole compound having a substituted phenyl substituent as shown in Formulas E and F are not completely understood. However, to further aid those skilled in the art to understand and practice that species of the invention, the proposed theoretical mechanism by which the advantageous results are thought to be effected will be discussed here. It should be understood, however, that the diffusion transfer photographic system has been proved to be operative and highly effective through extensive experimentation and the proposed theoretical mechanism is not to be construed as being limiting of the invention.

It is theorized that such advantageous results are obtainable because the compounds which are released as a result of the cleavage of the blocking moiety during processing perform different functions at different stages of the development process, that is, as weak silver solvents and promoters of development at one stage of the development process and as development restrainers, or inhibitors, at another stage of the process, and that the dual functions of these compounds within the diffusion transfer photographic system are pH dependent.

It is well known that in the diffusion transfer development process the pH of any particular location within the film unit varies with time. Typically, the processing composition employed in the process has a very high pH, e.g., from about 13-14 and during the development process each layer of a multilayer film unit goes through a broad pH range which includes very high pH levels and relatively low pH levels. When the pH is substantially equal to or above the pKa of the substituent $R_9$ on the phenyl ring, the dianion is formed, for example,

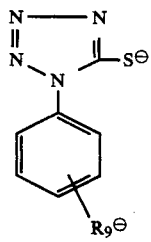

and acts as a weak silver solvent to form relatively soluble silver salts, thus promoting development. When the pH falls below the pKa of the substituent $R_9$, the monoanion is formed, for example,

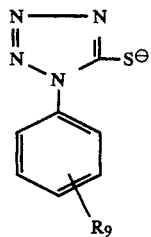

and the silver salt of the monoanion of the compound is very low in solubility resulting in a development restrainer action.

In view of the foregoing, it will be understood that when it is desired to utilize both functions, development of the exposed photosensitive element in the presence of such compounds is carried out with a processing composition having a pH substantially equal to or above the pKa of the particular substituent, at least for some period of time, when the processing composition comes into contact with the compound so as to enable the blocking moiety to cleave and the substituent ($R_9$) to ionize to form the dianion. In addition, at some point during the development process, the pH of the environment where the compound is located will go below the pKa of the substituent so as to enable the monoanion to be formed again.

The compounds utilized according to the invention may be used in conjunction with any photographic emulsion. In a preferred embodiment the compounds are utilized in diffusion transfer photographic systems, particularly those which include a negative working silver halide emulsion, i.e., one which develops in the areas of exposure. Further, these compounds may be used in association with any image dye-providing materials. In a particularly preferred embodiment the diffusion transfer photographic film elements of the invention include one or more image dye-providing materials which may be initially diffusible or nondiffusible. In diffusion transfer photographic systems the image dye-providing materials which can be utilized generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers. The requisite differential in mobility or solubility may be obtained, for example, by a chemical reaction such as a redox reaction, a coupling reaction or a cleavage reaction. In a particularly preferred embodiment of the invention the image dye-providing materials are dye developers which are initially diffusible materials. The dye developers contain, in the same molecule, both the chromophoric system of a dye and a silver halide developing function as is described in U.S. Pat. No. 2,983,606. Other image dye-providing materials which may be used include, for example, initially diffusible coupling dyes such as are useful in the diffusion transfer process described in U.S. Pat. No. 3,087,817 which are rendered nondiffusible by coupling with the oxidation product of a color developer; initially nondiffusible dyes which release a diffusible dye following oxidation, sometimes referred to as "redox dye releaser" dyes, described in U.S. Pat. Nos. 3,725,062 and 4,076,529; initially nondiffusible image dye-providing materials which release a diffusible dye following oxidation and intramolecular ring closure as are described in U.S. Pat. No. 3,443,939 or those which undergo silver assisted cleavage to release a diffusible dye in accordance with the disclosure of U.S. Pat. No. 3,719,489; and initially nondiffusible image dye-providing materials which release a diffusible dye following coupling with an oxidized color developer as described in U.S. Pat. No. 3,227,550. The effect obtained upon any individual image dye-providing material will be dependent at least in part, upon the distance between the compound and the image dye-providing material in the film unit.

The compounds may be incorporated into the photographic elements by any suitable technique. The compounds can be incorporated in the photographic element typically by being coated from a water or oil dispersion and the layer(s) in which they reside typically include a binder material such as gelatin or the like.

In a preferred embodiment of the invention, the compounds are utilized in diffusion transfer photographic film units in conjunction with initially diffusible dye developers as the image dye-providing materials. As described in U.S. Pat. No. 2,983,606 a photosensitive element containing a dye developer and silver halide emulsion is photoexposed and a processing composition applied thereto, for example, by immersion, coating spraying, flowing, etc., in the dark. The exposed photosensitive element is superposed prior to, during, or after the processing composition is applied, on a sheet-like support element which may be utilized as an image-receiving element. In a preferred embodiment, the processing composition is applied to the exposed photosensitive element in a substantially uniform layer as the photosensitive element is brought into superposed relationship with the image-receiving layer. The processing composition, positioned intermediate the photosensitive element and the image-receiving layer, permeates the emulsion to initiate development. The dye developer is immobilized or precipitated in exposed areas as a consequence of the development. In unexposed and partially exposed areas of the emulsion, the dye developer is unreacted and diffusible and thus provides an imagewise distribution of unoxidized dye developer, diffusible in the processing composition, as a function of the point-to-point degree of exposure of the silver halide emulsion. At least part of this imagewise distribution of unoxidized dye developer is transferred, by imbibition, to a superposed image-receiving layer or element, said transfer substantially excluding oxidized dye developer. The image-receiving layer receives a depthwise diffusion, from the developed emulsion, of unoxidized dye developer without appreciably disturbing the imagewise distribution thereof to provide a reversed or positive color image of the developed image. The image-receiving element may contain agents adapted to mordant or otherwise fix the diffused, unoxidized dye developer. In a preferred embodiment of said U.S. Pat. No. 2,983,606 and in certain commercial applications thereof, the desired positive image is revealed by separating the image-receiving layer from the photosensitive element at the end of a suitable imbibition period. Alternatively, as also disclosed in said U.S. Pat. No. 2,983,606, the image-receiving layer need not be separated from its superposed contact with the photosensitive element, subsequent to transfer image formation, if the support for the image-receiving layer, as well as any other layers intermediate said support and image-receiving layer, is transparent and a processing composition containing a substance, e.g., a white pigment, effective to mask the developed silver halide emulsion or emulsions is applied between the image-receiving layer and said halide emulsion or emulsions.

Dye developers, as noted in said U.S. Pat. No. 2,983,606, are compounds which contain, in the same molecule, both the chromophoric system of a dye and also a silver halide developing function. By "a silver halide developing function" is meant a grouping adapted to develop exposed silver halide. A preferred silver halide development function is a hydroquinonyl group. In general, the development function includes a benzenoid developing function, that is, an aromatic developing group which forms quinonoid or quinone substances when oxidized.

Multicolor images may be obtained using dye developers in diffusion transfer processes by several techniques. One such technique contemplates obtaining multicolor transfer image utilizing dye developers by employment of an integral multilayer photosensitive element, such as is disclosed in the aforementioned U.S. Pat. Nos. 2,983,606 and 3,345,163, wherein at least two selectively sensitized photosensitive strata, superposed on a single support, are processed, simultaneously and without separation, with a single common image-receiving layer. A suitable arrangement of this type comprises a support carrying a red-sensitive silver halide emulsion stratum, a green-sensitive silver halide emulsion stratum and a blue-sensitive silver halide emulsion stratum, said emulsions having associated therewith, respectively for example, a cyan dye developer, a magenta dye developer and a yellow dye developer. The dye developer may be utilized in the silver halide emulsion stratum, for example, in the form of particles, or it may be disposed in a stratum behind the appropriate silver halide emulsion strata. Each set of silver halide emulsion and associated dye developer strata may be separated from other sets by suitable interlayers, for example, by a layer or stratum of gelatin or polyvinyl alcohol. In certain instances, it may be desirable to incorporate a yellow filter in front of the green-sensitive emulsion and such yellow filter may be incorporated in an interlayer. However, where desirable, a yellow dye developer of the appropriate spectral characteristics and present in a state capable of functioning as a yellow filter may be so employed and a separate yellow filter omitted.

Particularly useful products for obtaining multicolor dye developer images are disclosed in U.S. Pat. No. 3,415,644. This patent discloses photographic products wherein a photosensitive element and an image-receiving layer are maintained in fixed relationship prior to exposure, and this relationship is maintained as a laminate after processing and image formation. In these products, the final image is viewed through a transparent (support) element against a light-reflecting, i.e., white background. Photoexposure is made through said transparent element and application of the processing composition provides a layer of light-reflecting material to provide a white background. The light-reflecting material (referred to in said patent as an "opacifying agent") is preferably titanium dioxide, and it also performs an opacifying function, i.e., it is effective to mask the developed silver halide emulsions so that the transfer image may be viewed without interference therefrom, and it also acts to protect the photoexposed silver halide emulsions from post-exposure fogging by light passing through said transparent layer if the photoexposed film unit is removed from the camera before image formation is completed.

U.S. Pat. No. 3,647,437 is concerned with improvements in products and processes disclosed in said U.S. Pat. No. 3,415,644, and discloses the provision of light-absorbing materials to permit such processes to be preformed, outside of the camera in which photoexposure is effected, under much more intense ambient light conditions. A light-absorbing material or reagent, preferably a pH-sensitive phthalein dye, is provided so positioned and/or constituted as not to interfere with photoexposure but so positioned between the photoexposed silver halide emulsions and the transparent support during processing after photoexposure as to absorb light which otherwise might fog the photoexposed emulsions. Furthermore, the light-absorbing material is so positioned and/or constituted after processing as not to interfere with viewing the desired image shortly after said image has been formed. In the preferred embodiments, the light-absorbing material, also sometimes referred to as an optical filter agent, is initially contained in the processing composition together with a light-reflecting material, e.g., titanium dioxide. The concentration of the light-absorbing dye is selected to provide the light transmission opacity required to perform the particular process under the selected light conditions.

In a particularly useful embodiment, the light-absorbing dye is highly colored at the pH of the processing composition, e.g., 13–14, but is substantially non-absorbing of visible light at a lower pH, e.g., less than 10–12. This pH reduction may be effected by an acid-reacting reagent appropriately positioned in the film unit, e.g., in a layer between the transparent support and the image-receiving layer.

The dye developers are preferably selected for their ability to provide colors that are useful in carrying out subtractive color photography, that is, the previously mentioned cyan, magenta and yellow. The dye developers employed may be incorporated in the respective silver halide emulsion or, in the preferred embodiment, in a separate layer behind the respective silver halide emulsion, and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Other diffusion transfer products and processes in which the dye developers of the present invention may be utilized are described in U.S. Pat. Nos. 3,573,043 and 3,594,165. For convenience, the entire disclosure of each of the six patents referred to immediately above is hereby incorporated by reference herein.

In one embodiment of a film unit according to the invention the photosensitive element includes a light reflecting layer between the silver halide layer and the image dye-providing material layer (as described in Canadian Pat. No. 668,592), the substrate of the photosensitive element carries the polymeric acid neutralizing layer which in turn carries the timing layer (as described in U.S. Pat. No. 3,573,043) and the processing composition includes an oximated polydiacetone acrylamide thickening agent (as described in U.S. Pat. No. 4,202,694).

In another embodiment wherein a diffusion transfer film unit includes a compound within Formula A wherein PHOTO is a moiety within Formulas C-F, the compound is incorporated in the photosensitive element in a layer between the support of the element and the silver halide emulsion closest to that support. This structure combines a delay in the cleavage of the compound with a delay in the diffusion of the released restrainer moiety through the film unit. In another embodiment a development restrainer precursor according to the invention is incorporated in the photosensitive element and the film unit is processed with a processing composition which includes 1-(4-hydroxyphenyl)-1H-tetrazole-5-thiol.

The invention will now be described further in detail with respect to specific preferred embodiments by way of examples, it being understood that these are illustrative only and the invention is not intended to be limited to the materials, conditions, process parameters, etc. which are recited therein.

EXAMPLE I

A solution of 1-phenyl-5-mercaptotetrazole (37.42 g; 0.21 mole) in 250 ml of dry acetone (kept over molecular sieves 4A) was stirred with sodium bicarbonate (17.64 g; 0.21 mole) under nitrogen for 15 minutes. 1,3-Dichloro-2-propanone (12.7 g; 0.1 mole) was added and the reaction mixture heated under reflux with stirring for 5 hours. The cooled reaction mixture was filtered and the solid (A) collected. The filtrate was stripped of solvent on the rotary evaporator and the residual solid (B) combined with solid (A). The combined solids were stirred with an aqueous solution of sodium bicarbonate (8 g) in 300 ml of water for 20 minutes, collected again by filtration, washed well with water and dried in a vacuum oven, first at ambient temperature and then at 50° C. to give 39.0 g (95% yield) of a compound represented by the formula

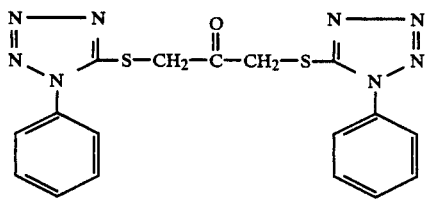

m.p. 152°–154° C., which gave a single spot on TLC (chloroform; Whatman K5F Silica Gel).

The structure was confirmed by PMR and IR spectra.

EXAMPLE II

The Ketone from Example 1 (12.3 g; 0.03 mole) was dissolved in a mixture of tetrahydrofuran (200 ml) and methanol (50 ml) with heating. Hydroxylamine hydrochloride (2.3 g; 0.033 mole), potassium acetate (3.24 g; 0.033 mole) and water (20 ml) were added and the reaction mixture heated under reflux for 20 hours. The solvent was removed on a rotary evaporator and the syrupy residue diluted with methanol until a white crystalline solid formed. The mixture was diluted with ice water, stirred for 15 minutes and the solid collected by filtration, washed well with water and dried in vacuum oven first at ambient temperature and then at 50° C. to give 12.35 g of compound III, m.p. 145°–147° C. which gave a single spot on TLC (5% ethyl acetate/95% chloroform; Whatman K5F silica gel).

The structure of the compound was confirmed by PMR and IR spectra.

EXAMPLE III

A solution of potassium hydroxide [26.13 g of 45% w/w aqueous potassium hydroxide (SO-P-236 from Fisher Scientific Co.) diluted with 70 ml of methanol] was added to a solution of 1-(4-hydroxyphenyl)-1H-tetrazole-5-thiol (40.8 g; 0.21 mole) in 200 ml of methanol with stirring under nitrogen. The solution was stirred for 20 minutes and 1,3-dichloro-2-propanone (12.7 g; 0.1 mole) was added in three portions with stirring over 15 minutes and the stirring continued for 4 hours. A solution of sodium bicarbonate (4.2 g) in 200 ml of water was added to the reaction mixture and stirring continued for an additional 15 minutes. Further dilution with water (two 400 ml volumes) with stirring and cooling in an ice bath resulted in the separation of a solid which was collected by filtration, washed with water and dried in a vacuum oven at ambient temperature to a constant weight (44.0 g; quantitative yield). The solid was recrystallized from a methanol/water solution to give 40 g of a beige colored solid, m.p. 124°–125° C. (dec), represented by the formula

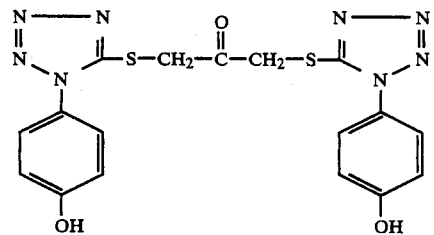

The compound gave a single spot on TLC (10% methanol/90% chloroform; Whatman K5F silica gel). The structure of the compound was confirmed by PMR, CMR, IR and UV spectra.

EXAMPLE IV

Hydroxylamine hydrochloride (7.64 g; 0.11 mole); potassium acetate (10.8 g; 0.11 mole) and water (44 ml) were added to a solution of the ketone shown in Example III (44.2 g; 0.1 mole) in 220 ml of methanol and the reaction mixture heated under reflux with stirring for 2 hours. The reaction mixture was cooled in an ice bath and then diluted five times with 200 ml volumes of water with stirring. The resulting solid was collected by filtration, washed with water and dried, first in air and then in a vacuum oven at ambient temperature, to a constant weight (42.81 g, 94% yield).

The solid was dissolved in 120 ml of hot methanol and decolorizing carbon (Norit A, 4 g) and diatomaceous earth (Celite, 4 g) were added. The mixture was heated on a steam bath for 20 minutes, filtered through a diatomaceous earth pad and washed with 50 ml of methanol. The combined filtrate was concentrated to about 120 ml, cooled in an ice bath and diluted gradually with water (three 20 ml volumes) with vigorous stirring. The precipitated solid was collected by filtration and dried to a constant weight in a vacuum oven at ambient temperature to give 37.8 g of compound I m.p. 183°–5° C.

The compound gave a single spot on TLC (10% methanol/90% chloroform; Whatman K5F silica gel). The structure was confirmed by PMR, CMR, IR and UV spectra.

Compound I was also made by the following procedure: the tetrazole (40.8 g, 0.21 mole) was dissolved in 200 ml of methanol and a potassium hydroxide solution [26.13 g of 45% w/w aqueous potassium hydroxide (SO-P-236 from Fisher Scientific Co.) diluted with 70 ml of methanol] was added with stirring under nitrogen. The solution was stirred for 20 minutes. 1,3-Dichloro-2-propanone (12.7 g; 0.1 mole) was added in three portions with stirring over 15 minutes and the stirring continued for 4 hours. Hydroxylamine hydrochloride (7.64 g, 0.11 mole) and potassium acetate (10.8 g; 0.11 mole) were added to the reaction mixture which was then heated under reflux for 2 hours. The reaction mixture was cooled to room temperature and the pH adjusted to approximately 8 with 10.8 g of 45% (w/w) aqueous potassium hydroxide diluted with 40 ml of water and 18 g of solid sodium bicarbonate. Gradual dilution with water (six 200 ml volumes) with stirring resulted in the precipitation of a solid which was collected by filtration, washed with water and dried in air to yield 40.35 g of product. Recrystallization from methanol/water as described above in this Example gave 34 g of compound I, m.p. 183°–185° C. (dec). The compound gave a single spot on TLC and its spectral properties were identical in all respects with the sample of compound I obtained above.

EXAMPLE V

P-toluenesulfonhydrazide (1.86 g, 0.01 mole) was added to a solution of 1,3-bis[1-(4-hydroxyphenyl) tetrazolyl-(5)-mercapto-2-propanone] (2.21 g; 0.005 mole) in 60 ml of glacial acetic acid in portions with stirring over 10 minutes and stirring continued at ambient temperature overnight. The reaction mixture was poured into 400 ml of water and stirred for 30 minutes. The resulting white solid was collected by filtration, washed with water and dried, first in air and then in a vacuum oven at 60° C., to a constant weight, 2.77 g, 91% yield, of compound II.

The compound fused and shrank at 98°–100° C. and melted with decomposition at 160°–163° C. It gave a single spot on TLC (10% methanol/ 90% chloroform; K5F Whatman silica gel). The structure of the compound was confirmed by a PMR spectrum.

EXAMPLE VI 1-(4-Acetylphenyl)-5-mercaptotetrazole (23.13 g; 0.105 mole) and 1,3-dichloro-2-propanone (6.35 g; 0.05 mole) were condensed in accordance with the procedure described in Example III to give 18.94 g (77% yield) of the triketone compound, m.p. 155°–156° C. which gave a single spot on TLC. The structure was confirmed with an IR spectrum.

The triketone was oximated with hydroxylamine hydrochloride and sodium acetate in methanol to give compound IV, m.p. 170°–171° C. The structure of the compound was confirmed by IR and PMR spectra.

EXAMPLE VII

A mixture of 1-(hydroxyphenyl)-1H-tetrazole-5-thiol (9.71g, 0.05 mole), chloroacetone [4.63 g (about 90% pure), 0.045 mole] and sodium bicarbonate (4.20 g, 0.05 mole) in 100 ml of dry acetonitrile was stirred under nitrogen at ambient temperature for 20 hours. The reaction mixture was filtered and the salts washed with fresh acetonitrile. The filtrate was stripped of solvent on a rotary evaporator and the resulting light tan crystals were recrystallized from methanol followed by drying in a vacuum oven at ambient temperature to give 4.43 g (35% yield) of off-white crystals represented by the formula

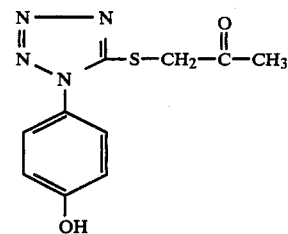

m.p. 145°–146° C.

The structure of the compound was confirmed by IR, UV and PMR spectra. TLC (5% EtOAc/95% CHCl₃, Whatman K5F silica gel) gave a single spot.

EXAMPLE VIII

A mixture of the ketone intermediate of Example VII (4.0 g; 0.016 mole), hydroxylamine hydrochloride (1.22 g; 0.0175 mole) and sodium acetate (1.36 g; 0.0175 mole) in 100 ml of absolute ethanol was stirred at ambient temperature for 20 hours. After 125 ml of water was added the mixture was stirred for 15 minutes and then stored overnight in a refrigerator. The resultant white solid was recovered by filtration, washed with water and dried in a vacuum oven at ambient temperature to give 3.48 g (82% yield) of compound V, m.p. 191°–192° C.

TLC as described above gave a single spot. The structure of the compound was confirmed by IR, UV and PMR spectra.

EXAMPLE IX

A mixture of 1-(4-acetylphenyl)-1H-tetrazole-5-thiol (11.01 g, 0.05 mole), chloroacetone [4.63 g (about 90% pure), 0.045 mole] and sodium bicarbonate (4.20 g, 0.05 mole) in 100 ml of dry acetonitrile was stirred under nitrogen at ambient temperature for 20 hours. The reaction mixture was filtered and the salts washed with fresh acetonitrile. The solvent was stripped from the filtrate on a rotary evaporator and the solid was recrystallized from methanol followed by drying in a vacuum oven at ambient temperature to give 7.09 g (51% yield) of bronze colored cyrstals represented by the formula

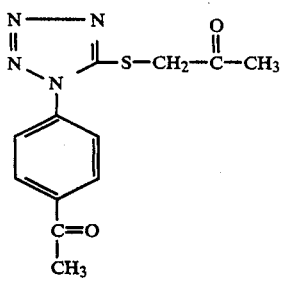

m.p. 126°–127° C.

TLC as described above gave a single spot. The structure of the compound was confirmed by IR, UV and PMR spectra.

EXAMPLE X

A mixture of the ketone intermediate from Example IX (5.53 g, 0.02 mole), hydroxylamine hydrochloride (3.042 g, 0.042 mole) and sodium acetate (3.40 g, 0.042 mole) in 100 ml of absolute ethanol was stirred at ambient temperature for 20 hours. After water (125 ml) was added the mixture was stored overnight in a refrigerator. The resulting tan colored solid was collected by filtration, washed with water and dried in a vacuum oven at ambient temperature to give 5.43 g (89% yield) of compound VI, m.p. 165°–167° C.

TLC as described above gave a single spot. The structure of the compound was confirmed by IR, UV and PMR spectra.

EXAMPLE XI

A solution of phenacyl bromide (10 g, 0.005 mole) in 50 ml of methanol was mixed with a solution of hydroxylamine sulfate (4.1 g, 0.025 mole) in 50 ml of water. After 1 day the methanol was removed under vacuum and the residue extracted with toluene. The water was separated and the organic phase was dried over sodium sulfate. The solvent was removed under vacuum and the residue was crystallized from a mixture of chloroform and petroleum ether and dried to give 4.9 of a fluffy white solid represented by the formula

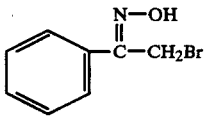

m.p. 96°–97° C. The structure of the compound was confirmed by PMR and CMR spectra.

The sodium salt of 1-(4-phenyl)-1H-tetrazole-5-thiol and the previous product (2.14 g, 0.010 mole) were stirred in 10 ml of dry dimethylformamide for 1 day. The reaction mixture was poured into 400 ml of water and the resulting white gumming material collected and dissolved in chloroform. The solution was washed with water and dried over sodium sulfate. The chloroform solution was slowly diluted with petroleum ether and the white solid which crystallized was collected by filtration, washed with petroleum either and dried to give compound VII, m.p. 159°–161° C.

The structure of the compound was confirmed by PMR and CMR spectra.

EXAMPLE XII

A mixture of 1-(4-phenyl)-1H-tetrazole-5-thiol (9.0 g, 0.0505 mole), bromoacetaldehyde diethyl acetal (9.85 g, 0.05 mole), sodium bicarbonate (4.3 g, 0.051 mole) and potassium iodide (0.88 g, 0.005 mole) in 100 ml of acetonitrile was heated at reflux under nitrogen for 6 hours. The reaction mixture was cooled to room temperature and the salts removed by filtration using fresh acetonitrile for the washings. The solvent was stripped from the filtrate to give a dark colored residue which was stirred in a mixture of 100 ml of methylene chloride and aqueous sodium bicarbonate for 15 minutes. The organic phase was separated, treated with charcoal and filtered through a diatomaceous earth pad. The filtrate was washed with water and brine and dried over anhydrous sodium sulfate. The solvent was removed on a rotary evaporator to give 10.83 g of a syrupy residue. Dilution with hexane and cooling induced cyrstallization. The solid was removed by filtration and dried in a vacuum oven to give 8.15 g of a compound represented by the formula

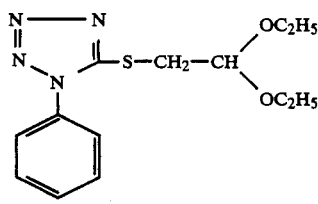

m.p. 42°–44° C.

TLC as described above gave a single spot. The structure of the compound was confirmed by a PMR spectrum.

EXAMPLE XIII

The diethyl acetal from Example XII (2.94 g, 0.01 mole) and hydroxylamine hydrochloride (0.72 g, 0.0103 mole) were heated under reflux in a mixture of ethanol (30 ml) and water (10 ml) for one hour. The reaction mixture was cooled and sodium acetate trihydrate (1.36 g, 0.01 mole) added followed by heating under reflux for an additional hour. The solvent was removed on a rotary evaporator and the residue diluted with water and then extracted with ethyl acetate. The extract was washed with brine and dried over anhydrous sodium sulfate. Removal of the solvent gave a syrup which on trituration with ether turned to a crystalline solid. The solid was recovered by filtration, washed with ether and dried in a vacuum oven to give 1.23 g of compound VIII, m.p. 85°–86° C. which gave a single spot on TLC. The structure of the compound was confirmed by IR and PMR spectra.

EXAMPLE XIV

A mixture of 1-(4-phenyl)-1H-tetrazole-5-thiol (8.91 g, 0.05 mole), chloroacetone [4.63 g (about 90% pure), 0.045 mole] and sodium bicarbonate (4.2 g, 0.05 mole) in 100 ml of dry acetonitrile was stirred under nitrogen at ambient temperature for 66 hours. The reaction mixture was filtered and the salts washed with fresh acetonitrile.

The combined filtrate was stripped off solvent on a rotary evaporator and the residual off-white solid was recrystallized from methanol followed by drying in a vacuum oven at ambient temperature to give 8.92 g (76% yield) of white crystals, m.p. 77°–78° C. which gave a single spot on TLC.

The structure of the compound was confirmed by IR, UV and PMR spectra.

EXAMPLE XV

A mixture of the ketone intermediate from Example XIV (4.69 g, 0.02 mole), hydroxylamine hydrochloride [1.52 g (about 96% pure), 0.021 mole] and sodium acetate (1.72 g, 0.021 mole) in 100 ml of absolute ethanol was stirred at ambient temperature for one week. The resulting colorless crystals were recovered by filtration, washed with ethanol and dried in a vacuum oven at ambient temperature to give 4.34 g of compound IX. Recrystallization of 4 g from aqueous methanol gave 2.30 g (52% yield) of colorless needless, m.p. 141°–142° C. which gave a single spot on TLC.

The structure of the compound was confirmed by IR, UV and PMR spectra.

EXAMPLE XVI

The oxime of p-methoxy-α-bromo acetophenone (2.5 g, (0.0102 mole) and the sodium salt of 1-(4-phenyl)-1H-tetrazole-5-thiol (2.1 g, 0.0105 mole) were stirred in 10 ml of dry dimethylformamide for 18 hours. The reaction mixture was poured into 200 ml of water and the resulting solid collected by filtration and recrystallized from a mixture of chloroform and petroleum ether to give compound X.

EXAMPLE XVII

P-(methyl sulfonamido)-α-bromo acetophenone (39 g, 0.133 mole) and hydroxylamine sulfate (21.8 g, 0.133 mole) were slurried in 600 ml of ethanol and 20 ml of water at 45° C. for 1 day. The reaction mixture was cooled to room temperature and the solid removed by filtration. The filtrate was poured slowly into 1500 ml of warm water and the resulting white solid collected by filtration, washed well with water and dried to give 25 g (61% yield) of the oxime intermediate.

The structure was confirmed by PMR and CMR spectra.

The oxime of p-(methylsulfonamido)-α-bromo acetophenone (24 g, 0.078 mole) and the sodium salt of 1-(4-phenyl)-1H-tetrazole-5-thiol (15.7 g, 0.0785 mole) were stirred in 120 ml of dimethylformamide for 18 hours. The solution was poured into 1000 ml of water and the resulting solid, collected, washed with water and dried. The crude product was crystallized from aqueous acetone to give 10 g of white crystals, compound XI, which were assigned as the anti isomer based on CMR and PMR.

EXAMPLE XVIII

Tosyl hydrazide (8.8 g, 0.047 mole) was added to a solution of phenacyl bromide (10 g, 0.050 mole) in 120 ml of ether and the resulting suspension was stirred for 20 hours. The resulting solid was collected by filtration, washed with fresh ether and dried to give 13.4 g (78% yield) of a white solid represented by the formula

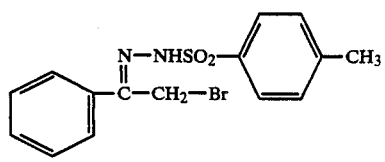

m.p. 137°–138° C. The structure of the compound was confirmed by PMR and CMR spectra.

The sodium salt of 1-(4-phenyl)-1H-tetrazole-5-thiol was added to a solution of the previous product (0.77 g, 0.0021 mole) in 5 ml of dry dimethylformamide and the solution stirred overnight. The reaction mixture was poured into 200 ml of ice water and the resulting white solid was collected by filtration, washed and dried to give 0.8 g of compound XII.

The structure of the compound was confirmed by PMR and CMR spectra.

EXAMPLE XIX

As a control, a film unit was prepared as follows: the photosensitive element comprised an opaque subcoated polyester film base upon which there were coated the following layers in succession:

1. as a polymeric acid layer approximately 9 parts of a ½ butyl ester of polyethylene/maleic anhydride copolymer and 1 part polyvinyl butyral coated at a coverage of about 26372 mgs/m²;

2. a timing layer coated at a coverage of about 6000 mgs/m² comprising a 40/40/18/1.85 tetrapolymer of butyl acrylate/diacetone acrylamide/carbomethoxymethyl acrylate/acrylic acid;

3. a gelatin layer coated at a coverage of about 1200 mgs/m²;

4. an interlayer comprising about 3420 mgs/m² of a 60/29/6/4/0.4 pentapolymer of butyl acrylate/diacetone acrylamide/methacrylic acid/styrene/acrylic acid, about 180 mgs/m² of polyacrylamide and about 132 mgs/m² of monomethylol dimethyl hydantoin;

5. a gelatin layer coated at a coverage of about 300 mgs/m²;

6. a magenta dye developer layer comprising about 420 mgs/m² of a magenta dye developer represented by the formula

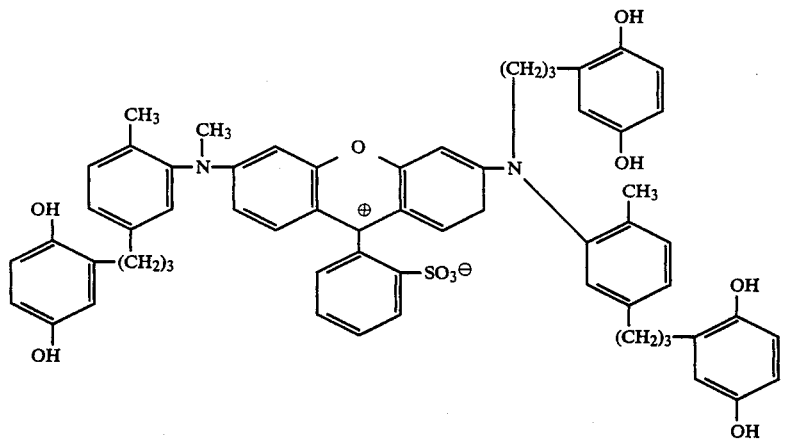

20 and about 538 mgs/m² of gelatin;

7. a green sensitive silver iodobromide emulsion layer comprising about 1130 mgs/m² of silver, about 756 mgs/m² of gelatin and about 258 mgs/m² of 4'-methyl phenyl hydroquinone;

8. a topcoat layer comprising about 323 mgs/m² of gelatin and about 27 mgs/m² of succindialdehyde.

The image receiving element comprised a 0.064 mm thick transparent subcoated polyester film base on which the following layers were coated in succession:

1. an image receiving layer coated at a coverage of about 300 mgs/ft² (3229 mgs/m²) of a graft copolymer comprised of 4-vinylpyridine (4VP) and vinyl benzyl trimethylammonium chloride (TMQ) grafted onto hydroxyethyl cellulose (HEC) at a ratio HEC/4VP/TMQ of 2.2/2.2/1 and about 4 mgs/ft² (43 mgs/m²) of 1,4-butanediol diglycidyl ether; and 2. an overcoat layer coated at a coverage of about 120 mgs/ft² (1292 mgs/m²) comprising 1 part of polyvinyl hydrogen phthalate, potassium salt and 1 part of a 1/1/0.35 mixture of Igepal CO-997 (nonylphenoxyethylene oxide ethanol), a 1/1/0.1/0.1 tetrapolymer of diacetone acrylamide/methacrylic acid/butyl acrylate/styrene, and 0.35 part of polyvinylpyrrolidone.

The film unit was processed with a processing composition made up as follows:

|  | GRAMS |
|---|---|
| Water | 1555.0 |
| Titanium dioxide | 2312.0 |
| Oximated polydiacetone acrylamide | 32.0 |
| Potssium hydroxide (45% aqueous solution) | 511.0 |
| Colloidal silica (30% aqueous dispersion) | 37.0 |
| N-phenethyl-α-picolinium bromide (50% solids) | 139.0 |
| 6-methyluracil | 14.1 |
| Hypoxanthine | 27.5 |
| 2-methylimidazole | 23.4 |
| 1-(4-hydroxyphenyl)-1H-tetrazole-5-thiol | 0.92 |

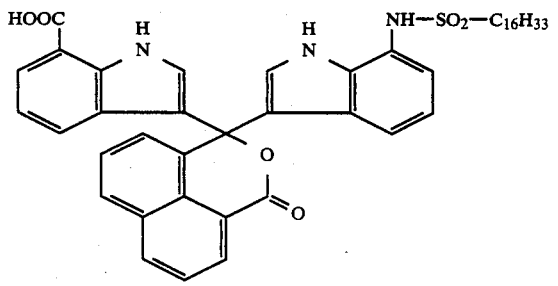

21.0

| | GRAMS |
|---|---|
| [chemical structure: bis-naphthol compound with OH, COOH groups, C18H27O substituent, and naphthalene lactone moiety] | 76.7 |

The photosensitive element was exposed (0.5 meter-candle-second) on a sensitometer to a test scale with green light through the topcoat layer and then brought together with the image-receiving element and processed by passing the film unit through a pair of rollers set at a gap spacing of about 0.0024 inch. The film unit was kept in the dark for 10 minutes and then read on a densitometer.

In addition, Film Unit A according to the invention was prepared. It was the same as the Control with the exception that the silver halide emulsion layer included about 140 mgs/m² of compound V. The film units were processed as described above at 45° F., 75° F. and 105° F.

| | | 45° F. | 75° F. | 105° F. |
|---|---|---|---|---|
| CONTROL | $D_{max}$ | 2.45 | 2.25 | 1.65 |
| | $D_{min}$ | 0.17 | 0.10 | 0.10 |
| | Speed | 1.21 | 1.45 | 1.77 |
| A | $D_{max}$ | 2.38 | 2.21 | 2.07 |
| | $D_{min}$ | 0.19 | 0.10 | 0.10 |
| | Speed | 1.13 | 1.31 | 1.37 |

It can be seen that the Control suffered a large loss in $D_{max}$ at 105° F. with a concomitant large speed increase with the same $D_{min}$. Film Unit A exhibited a relatively small $D_{max}$ loss at 105° F. with a small speed increase and the same $D_{min}$, thus indicating that the restrainer release material provided more uniform sensitometry over the temperature processing range.

EXAMPLE XX

The experiment of Example XIX was repeated with the exception that compound V was incorporated in the dye layer at the same coverage and was not present in the silver halide emulsion layer.

| | 45° F. | 75° F. | 105° F. |
|---|---|---|---|
| $D_{max}$ | 2.43 | 2.45 | 2.12 |
| $D_{min}$ | 0.24 | 0.19 | 0.15 |

| | 45° F. | 75° F. | 105° F. |
|---|---|---|---|
| Speed | 1.09 | 1.18 | 1.31 |

It can be seen that for this particular film unit, more uniform sensitometry was obtained when compound V was incorporated in the silver halide emulsion layer.

EXAMPLE XXI

As a control a film unit was prepared as follows: the photosensitive element comprised an opaque subcoated polyester film base uon which there were coated the following layers in succession:

Layers 1-5 were the same as layers 1-5 of the photosensitive element of Example XIX;

6. a magenta dye developer layer comprising about 420 mgs/m² of the magenta dye developer illustrated in Example XIX and about 538 mgs/m² of gelatin;

7. a layer comprising about 258 mgs/m² of 4'-methyl phenyl hydroquinone and about 538 mgs/m² of gelatin.

8. a green sensitive silver halide iodobromide emulsion layer comprising about 1130 mgs/m² of silver and about 497 mgs/m² of gelatin;

9. A topcoat layer comprising about 323 mgs/m² of gelatin and about 27 mgs/m² of succindialdehyde.

The image receiving element comprised a 0.064 mm thick transparent subcoated polyester film base on which the following layers were coated in succession:

1. an image receiving layer as described in Example XIX; and 2. a topcoat layer coated at a coverage of 85 mgs/ft² (915 mgs/m²) of 1 part Igepal CO-997 (nonylphenoxylethylene oxide ethanol), 1 part of a 1/1/0.1/0.1 tetrapolymer of diacetone acrylamide/methacrylic acid/butyl acrylate/styrene, and 0.35 part of polyvinylpyrolidone.

Film Unit B, according to the invention was prepared. This was the same as the Control with the exception that the magenta dye developer layer further included about 161/mgs/m² of compound VI.

The film unit was processed with a processing composition made up as follows:

| | GRAMS |
|---|---|
| Water | 1566.0 |
| Titanium dioxide | 2312.0 |
| Oximated polydiacetone acrylamide | 32.0 |
| Potssium hydroxide (45% aqueous solution) | 490.0 |
| Zonyl FSN | 23.5 |

| | | |
|---|---|---|
| Colloidal silica (30% aqueous dispersion) | | 37.0 |
| N-phenethyl-α-picolinium bromide (50% solids) | | 139.0 |
| 6-methyluracil | | 28.2 |
| Hypoxanthine | | 27.5 |
| 2-methylamidazole | | 23.4 |
| 1-(4-hydroxyphenyl)-1H-tetrazole-5-thiol | | 0.92 |
| 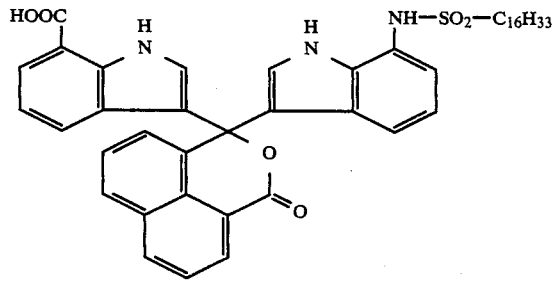 | | 21.0 |
| 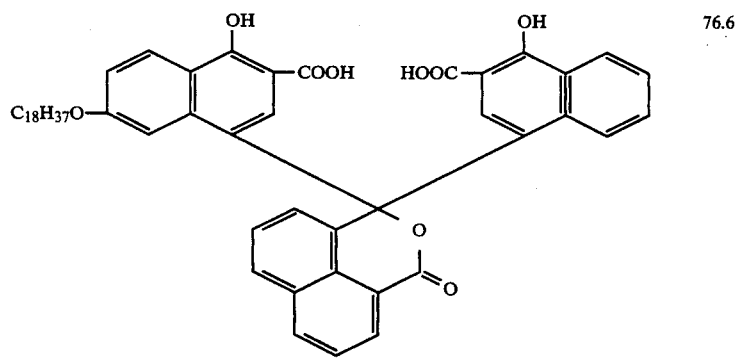 | | 76.6 |

| | | 45° F. | 75° F. | 105° F. |
|---|---|---|---|---|
| CONTROL | $D_{max}$ | 1.93 | 1.71 | 1.40 |
| | $D_{min}$ | 0.11 | 0.10 | 0.10 |
| | Speed | 1.35 | 1.54 | 1.76 |
| B | $D_{max}$ | 1.80 | 1.32 | 1.39 |
| | $D_{min}$ | 0.15 | 0.11 | 0.11 |
| | Speed | 1.31 | 1.53 | 1.65 |

It can be seen that the Control experienced a significant loss in $D_{max}$ at 105° F. with a corresponding speed increase with the same $D_{min}$. Film Unit B exhibited an increase in $D_{max}$ at 105° F. along with an increase in speed with the same $D_{min}$.

EXAMPLE XXII

As a control, a film unit was prepared as follows: the photosensitive element comprised an approximately 0.127 mm thick opaque subcoated polyethylene terephthalate photographic film base on which the following layers were coated in succession:

1. a polymeric acid layer comprising about 24,400 mgs/m² of a half butyl ester of ethylene maleic anhydride, about 4310 mgs/m² of polyvinyl butyral and about 89 mgs/m² of titanium dioxide;

2. a layer of styrene maleic anhydride copolymer coated at a coverage of about 400 mgs/m²;

3. a timing layer comprising a 40/40/18/2 tetrapolymer of butyl acrylate/diacetone acrylamide/carbomethoxymethyl acrylate/acrylic acid coated at a coverage of about 2000 mgs/m²;

4. a cyan dye developer layer comprising about 612 mgs/m² of a cyan dye developer represented by the formula

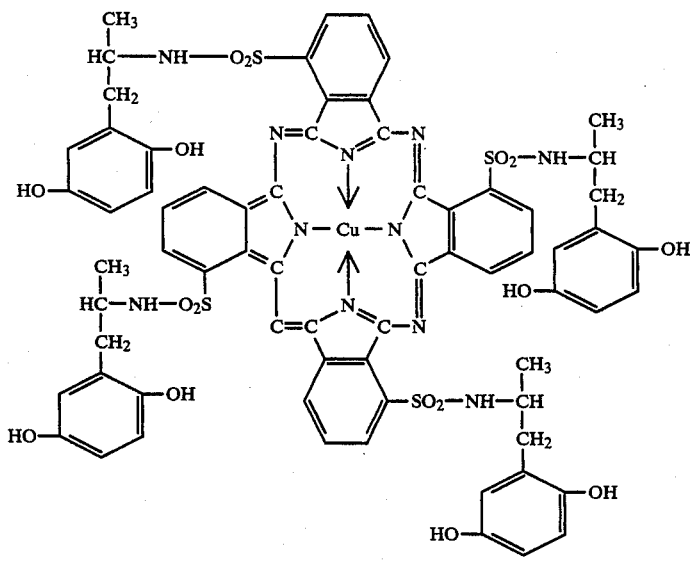

about 414 mgs/m² of gelatin and about 60 mgs/m² of 4'-meth phenyl hydroquinone (MPHQ);

5. a layer comprising about 1000 mgs/m² of titanium dioxide, about 375 mgs/m² of a 61/29/6/4/0.4 pentapolymer of butyl acrylate/diacetone acrylamide/methacrylic acid/styrene/acrylic acid, about 125 mgs/m² of gelatin and about 37.5 mgs/m² of polymethylmethacrylate;

6. a red sensitive silver iodobromide layer comprising about 967 mgs/m² of silver (1.5 microns), about 242 mgs/m² of silver (1.1 microns), about 725 mgs/m² of gelatin and about 60 mgs/m² of MPHQ;

7. an interlayer comprising about 3547 mgs/m² of the pentapolymer described in layer 5 and about 187 mgs/m² of polyacrylamide;

8. a magenta dye developer layer comprising about 420 mgs/m² of a magenta dye developer represented by the formula

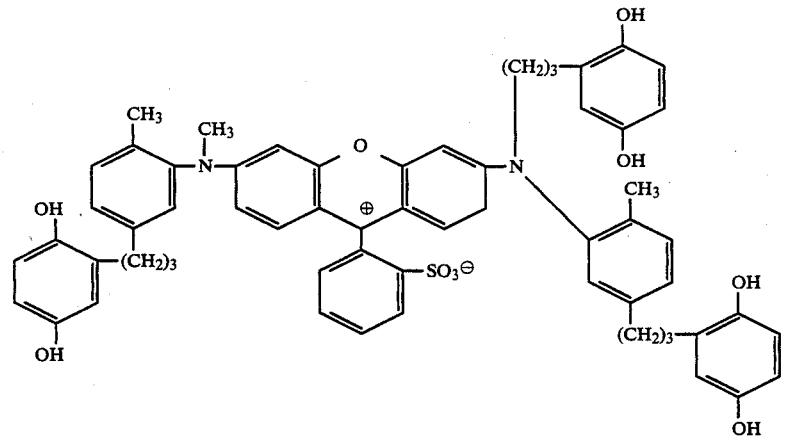

about 262 mgs/m² of gelatin and about 500 mgs/m² of 2-phenylbenzimidazole;

9. a layer comprising about 450 mgs/m² of Dow 620 (styrene-butadiene copolymer) latex and about 150 mgs/m² of gelatin;

10. a green sensitive silver halide emulsion layer comprising about 749 mgs/m² of silver (1.8 microns), about 615 mgs/m² of silver (1.1 microns), about 617 mgs/m² of gelatin and about 260 mgs/m² of MPHQ;

11. a layer comprising about 2459 mgs/m² of the pentapolymer described in layer 5, about 129 mgs/m² of polyacrylamide and about 700 mgs/m² of a scavenger represented by the formula

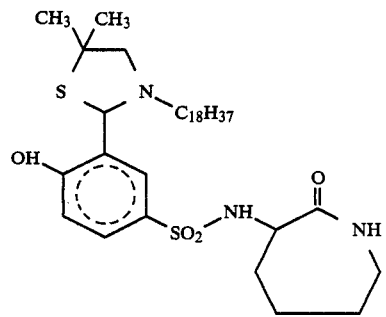

12. a layer comprising about 550 mgs/m² of benzidine yellow dye and about 165 mgs/m² of gelatin;

13. a yellow image dye-providing layer comprising about 1210 mgs/m² of a yellow image dye-providing material represented by the formula

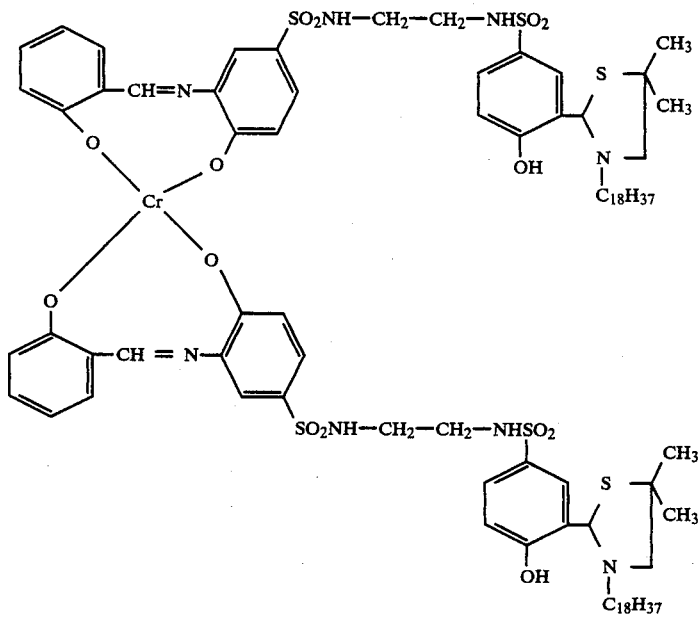

about 484 mgs/m² of gelatin and about 200 mgs/m² of Dow 620 latex;

14. a layer comprising about 490 mgs/m² of phenyl tertiarybutyl hydroquinone and about 245 mgs/m² of gelatin;

15. a blue sensitive silver iodobromide layer comprising about 174 mgs/m² of silver (1.6 microns), about 116 mgs/m² of silver (1.3 microns) and about 145 mgs/m² of gelatin; and 16. a gelatin layer coated at a coverage of about 800 mgs/m².

The image-receiving sheet comprised an approximately 0.069 mm thick polyester film base, including a small amount of an anti-light piping dye, upon which there were coated in succession:

1. an image-receiving layer coated at a coverage of about 300 mgs./ft.² (3229 mgs/m²) of a graft copolymer comprised of 4-vinylpyridine (4VP) and vinyl benzyl trimethylammonium chloride (TMQ) grafted onto hydroxyethyl cellulose (HEC) at ratio HEC/4VP/TMQ of 2.2/2.2/1 and about 4 mgs./ft² (43 mgs./m²) of 1,4-butanediol-diglycidyl ether; and 2. an overcoat layer coated at a coverage of about 85 mgs/ft² (915 mgs/m²) comprising 1 part Igepal CO-997 (nonylphenoxyethylene oxide ethanol), 1 part of a 1.0/1.0/0.1/0.1 tetrapolymer of methacrylic acid/diacetone acrylamide/butyl acrylate/styrene and 0.1 part of polyvinylpyrrolidone.

The film unit described above having both a dye developer and a thiazolidine image-dye providing material is described and claimed in commonly assigned application of Peter O. Kliem et al, Ser. No. 846,586, filed on even date herewith.

The film unit was processed with a processing composition made up as follows:

|  | GRAMS |
|---|---|
| Water | 1566.0 |
| Titanium dioxide | 2312.0 |
| Oximated polydiacetone acrylamide | 32.0 |
| Potassium hydroxide (50% aqueous solution) | 490.0 |
| Colloidal silica (30% aqueous dispersion) | 37.0 |
| Zonyl FSN (40% solids) | 23.5 |
| N-phenethyl-α-picolinium bromide (50% solids) | 139.0 |
| 6-methyluracil | 28.2 |
| 2-methylimidazole | 23.4 |
| Hypoxanthine | 27.5 |
| 1-(4-hydroxyphenyl)-1H-tetrazole-5-thiol | 0.92 |

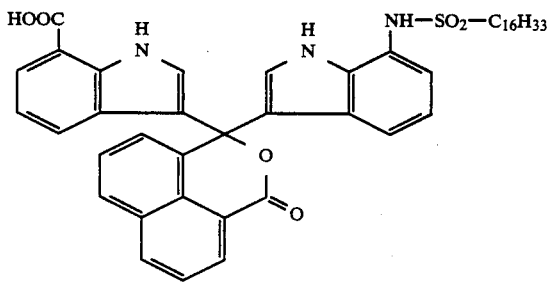

21.0

-continued

| | GRAMS |
|---|---|
| 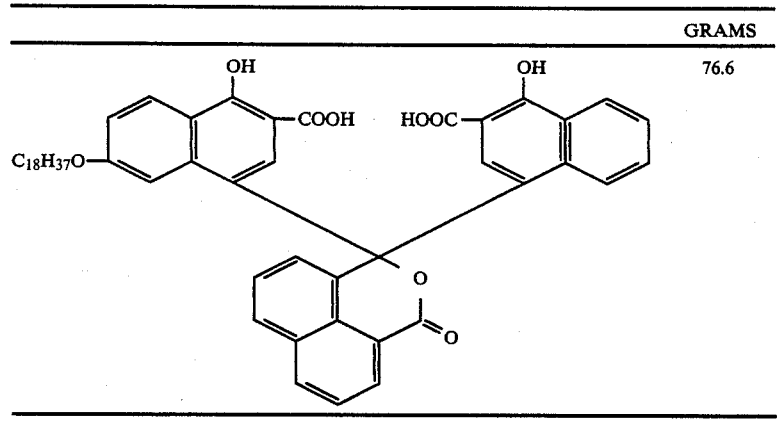 | 76.6 |

The film unit was exposed (0.5 meter-candle-second) through the transparent base of the image-receiving element on a sensitometer to a test exposure scale with white light and processed by passing the film unit through a pair of rollers at a gap spacing of about 0.0024 inch. Identical film units were processed at 55° F., 75° F. and 95° F. The neutral density columns of the images were read on a densitometer to obtain the $D_{max}$ and $D_{min}$ values for red, green and blue respectively. In addition the speeds of the red, green and blue curves respectively (defined as the negative log of the relative exposure required give red, green and blue absorption, respectively, in the neutral column a reflection density of 0.75) were measured.

Film units (C) according to the invention were prepared. These were identical with the Control with the exception that layers 4 and 8 each included about 60 mgs/m² of compound I; and layer 4 had about 1063 mgs/m² of silver (1.5 microns) and about 145 mgs/m² of silver (1.1 microns).

| FILM UNIT | | R | G | B | R | G | B |
|---|---|---|---|---|---|---|---|
| | | | 75° F. | | | | |
| CONTROL | $D_{max}$ | 1.90 | 1.97 | 1.72 | 1.43 | 1.46 | 1.65 |
| | $D_{min}$ | 0.08 | 0.11 | 0.12 | | | |
| C | $D_{max}$ | 1.85 | 1.93 | 1.98 | 1.48 | 1.55 | 1.60 |
| | $D_{min}$ | 0.09 | 0.09 | 0.12 | | | |
| | | | 55° F. | | | | |
| CONTROL | $D_{max}$ | 2.01 | 2.04 | 1.52 | 1.44 | 1.50 | 1.74 |
| | $D_{min}$ | 0.09 | 0.09 | 0.13 | | | |
| C | $D_{max}$ | 1.90 | 1.96 | 1.79 | 1.48 | 1.54 | 1.70 |
| | $D_{min}$ | 0.09 | 0.09 | 0.13 | | | |
| | | | 95° F. | | | | |
| CONTROL | $D_{max}$ | 1.20 | 1.75 | 1.67 | 1.53 | 1.45 | 1.66 |
| | $D_{min}$ | 0.10 | 0.15 | 0.13 | | | |
| C | $D_{max}$ | 1.28 | 1.66 | 1.97 | 1.52 | 1.58 | 1.61 |
| | $D_{min}$ | 0.09 | 0.11 | 0.13 | | | |

It can be seen that the red $D_{max}$ loss at 95° F. was smaller for Film Unit C than that of the Control.

Example XXIII

As a control a film unit was prepared as follows: the photosensitive element comprised an approximately 0.127 mm thick opaque subcoated polyethylene terephthalate photograph film base on which the following layers were coated in succession:

1. a polymeric acid layer comprising about 24, 795 mgs/m² of a half butyl ester of ethylene maleic anhydride, about 4375 mgs/m² of polyvinyl butyral and about 99 mgs/m² of titanium dioxide;

2. a layer of styrene maleic anhydride (including about 2% ethyl acetate) coated at a coverage of about 350 mgs/m²;

3. a timing layer comprising the tetrapolymer described in layer 3 of the photosensitive element of Example XXII coated at a coverage of about 2500 mgs/m²;

4. a cyan dye developer layer comprising about 612 mgs/m² of the cyan dye developer illustrated in Example XXII, about 359 mgs/m² of gelatin and about 61 mgs/m² of MPHQ;

5. a layer comprising about 1000 mgs/m² of titanium dioxide, about 375 mgs/m² of a 61/29/6/4/0.4 pentapolymer of butyl acrylate/diacetone acrylamide/methacrylic acid/styrene/acrylic acid, about 125 mgs/m² of gelatin, about 375 mgs/m² of polymethylmethacrylate and about 100 mgs/m² of polyacrylamide;

6. a red sensitive silver iodobromide layer comprising about 967 mgs/m² of silver (1.5 microns), about 242 mgs/m² of silver (1.1 microns), about 786 mgs/m² of gelatin and about 61 mgs/m² of MPHQ;

7. an interlayer comprising about 3420 mgs/m² of the pentapolymer described in layer 5, about 180 mgs/m² of polyacrylamide and about 132 mgs/m² of monomethylol dimethyl hydantoin;

8. a magenta dye developer layer comprising about 420 mgs/m² of the magenta dye developer illustrated in Example XXII, about 315 mgs/m² of gelatin and about 700 mgs/m² of 2-phenylbenzimidazole;

9. a layer comprising about 400 mgs/m² of Dow 620 (styrene-butadiene copolymer) latex, about 133 mgs/m² of gelatin and about 160 mgs/m² of MPHQ;

10. a green sensitive silver halide emulsion layer comprising about 750 mgs/m² of silver (1.8 microns), about 614 mgs/m² of silver (1.1 microns), about 730 mgs/m² of gelatin and about 100 mgs/m² of MPHQ;

11. an interlayer comprising about 2460 mgs/m² of the pentapolymer described in layer 5, about 130 mgs/m² of polyacrylamide, about 25 mgs/m² of succindialdehyde and about 700 mgs/m² of the scavenger illustrated in layer 11 of Example XXII;

12. a yellow filter dye layer comprising about 550 mgs/m² of benzidine yellow dye and about 275 mgs/m² of gelatin;

13. a yellow image dye-providing layer comprising about 1210 mgs/m² of the yellow thiazolidine image dye-providing material illustrated in layer 13 of Example XXII, about 484 mgs/m² of gelatin and about 200 mgs/m² of Dow 620 latex;

14. a layer comprising abut 490 mgs/m² of phenyl tertiarybutyl hydroquinone and about 245 mgs/m² of gelatin;

15. a blue sensitive silver iodobromide emulsion layer comprising about 174 mgs/m² of silver (1.6 microns), about 116 mgs/m² of silver (1.25 microns) and about 145 mgs/m² of gelatin; and 16. a gelatin layer coated at a coverage of about 800 mgs/m²;

The image-receiving sheet was the same as that described in Example XIX.

The film unit was processed with a processing composition made up as follows:

|  | WEIGHT PERCENT |
|---|---|
| Water | 40.75 |
| Titanium dioxide | 48.44 |
| Colloidal silica (30% aqueous dispersion) | 0.23 |
| Potassium hydroxide (50% aqueous solution) | 5.62 |
| N-phenethyl-α-picolinium bromide (50% solids) | 1.46 |
| 6-methyluracil | 0.59 |
| Oximated polydiacetone acrylamide | 0.67 |
| Hypoxanthine | 0.57 |
| 2-methylamidazole | 0.49 |
| Zonyl FSN (40% solids) | 0.20 |
| 1-(4-hydroxyphenyl)-1H-tetrazole-5-thiol | 0.019 |

The composition further included 0.44% and 1.50%, respectively, of the phthalein indicator dyes illustrated in Example XXII.

The film unit was processed as described in Example XXII. Identical film units were processed at 55° F., 75° F., 95° F., 105° F., and 115° F.

Film Units (D) according to the invention were made. These were identical to the Control with the exception that layer 4 included about 120 mgs/m² of compound I and had about 367 mgs/m² of gelatin; and layer 8 had 286 mgs/m² of gelatin and 500 mgs/m² of 2-phenylbenzimidazole.

| FILM UNIT | | R | G | B | R | G | B |
|---|---|---|---|---|---|---|---|
| | | | 55° F. | | | | |
| Control | $D_{max}$ | 1.62 | 1.85 | 1.46 | 1.65 | 1.74 | 1.84 |
| | $D_{min}$ | 0.08 | 0.07 | 0.12 | | | |
| D | $D_{max}$ | 1.64 | 1.74 | 1.42 | 1.61 | 1.77 | 1.87 |
| | $D_{min}$ | 0.09 | 0.08 | 0.12 | | | |
| | | | 75° F. | | | | |
| Control | $D_{max}$ | 1.71 | 1.90 | 1.77 | 1.69 | 1.71 | 1.70 |
| | $D_{min}$ | 0.08 | 0.09 | 0.11 | | | |
| D | $D_{max}$ | 1.76 | 1.84 | 1.71 | 1.57 | 1.70 | 1.66 |
| | $D_{min}$ | 0.09 | 0.10 | 0.12 | | | |
| | | | 95° F. | | | | |
| Control | $D_{max}$ | 1.49 | 1.74 | 1.84 | 1.74 | 1.70 | 1.66 |
| | $D_{min}$ | 0.09 | 0.11 | 0.13 | | | |
| D | $D_{max}$ | 1.69 | 1.71 | 1.77 | 1.52 | 1.70 | 1.69 |
| | $D_{min}$ | 0.11 | 0.12 | 0.13 | | | |
| | | | 105° F. | | | | |
| Control | $D_{max}$ | 1.24 | 1.61 | 1.75 | 1.76 | 1.68 | 1.74 |
| | $D_{min}$ | 0.10 | 0.13 | 0.14 | | | |
| D | $D_{max}$ | 1.48 | 1.58 | 1.80 | 1.50 | 1.75 | 1.71 |
| | $D_{min}$ | 0.11 | 0.12 | 0.16 | | | |
| | | | 115° F. | | | | |
| Control | $D_{max}$ | 0.96 | 1.38 | 1.47 | 1.91 | 1.76 | 1.89 |
| | $D_{min}$ | 0.11 | 0.15 | 0.15 | | | |
| D | $D_{max}$ | 1.30 | 1.32 | 1.46 | 1.47 | 1.82 | 1.88 |
| | $D_{min}$ | 0.12 | 0.13 | 0.19 | | | |

It can be seen that at the higher processing temperatures the Control suffered a large loss in red $D_{max}$ together with a sizable increase in red speed. Film Unit D, in comparison, exhibited a much smaller loss in red $D_{max}$ together with a much smaller red speed increase.

Although the invention has been decribed with respect to various embodiments thereof it is not intended to be limited thereto but rather those skilled in the art wil recognize that variations and modifications may be made therein which are within the spirit of the invention and the scope of the appended claims.

What is claimed is:

1. A compound represented by the formula

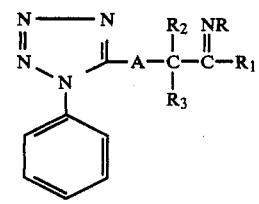

wherein A is sulfur or selenium; R is —OH, —OR₄, —NH₂, —NHR₅ or —NR₄R₆; R₁ is hydrogen, alkyl, —NH₂, phenyl or naphthyl; R₂ and R₃ are each independently hydrogen, alkyl, benzyl or phenyl; R₄ is —CONHR₇, —COR₇, —COOR₇ or —SO₂R₇; R₅ is —COR₇, —COOR₇ or —SO₂R₇; R₆ is —COR₇, —COOR₇ or —SO₂R₇; and R₇ is alkyl, phenyl, naphthyl, tolyl, benzyl or cyclohexyl.

2. A compound represented by the formula

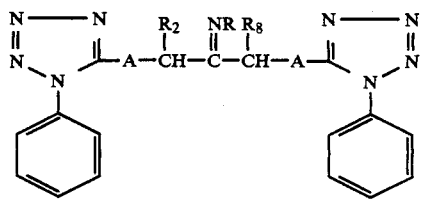

wherein A is sulfur or selenium; R is —OH, —OR₄, —NH₂, —NHR₅ or —NR₄R₆; R₂ and R₈ are the same and are hydrogen, alkyl, benzyl or phenyl; R₄ is —CONHR₇, —COR₇, —COOR₇ or —SO₂R₇; R₅ is —COR₇, —COOR₇ or —SO₂R₇; R₆ is —COR₇, —COOR₇ or —SO₂R₇; and R₇ is alkyl, phenyl, naphthyl, tolyl, benzyl or cyclohexyl.

3. A compound as represented by the formula

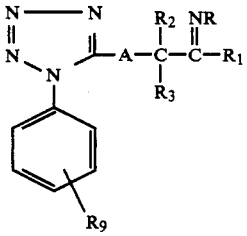

wherein A is sulfur or selenium; R is —OH, —OR₄, —NH₂, —NHR₅ or —NR₄R₆; R₁ is hydrogen, alkyl, —NH₂, phenyl or naphthyl; R₂ and R₃ each are independently hydrogen, alkyl, benzyl or phenyl; R₄ is —CONHR₇, —COR₇, —COOR₇ or —SO₂R₇; R₅ is —COR₇, —COOR₇ or —SO₂R₇; R₆ is —COR₇, —COOR₇ or —SO₂R₇; R₇ is alkyl, phenyl, naphthyl, tolyl, benzyl or cyclohexyl, and R₉ is —OH, —COCH₃, —OCOCH₃, —SO₂NH₂, —SO₂NHCH₃, —SO₂NHC₈H₁₇, —NHSO₂CH₃,

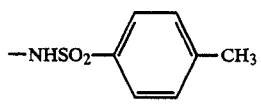

or $-\overset{\overset{NOH}{\|}}{C}-Z$, wherein Z is hydrogen, alkyl having from 1 to 10 carbon atoms, benzyl, phenethyl or phenyl.

4. A compound represented by the formula

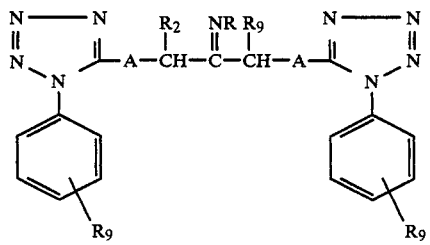

wherein A is sulfur or selenium; R is —OH, —OR₄, —NH₂, —NHR₅ or —NR₄R₆; R₂ and R₈ are the same and are hydrogen, alkyl, benzyl or phenyl; R₄ is —CONHR₇, —COR₇, —COOR₇ or —SO₂R₇; R₅ is —COR₇, —COOR₇ or —SO₂R₇; R₆ is —COR₇, —COOR₇ or —SO₂R₇; R₇ is alkyl, phenyl, naphthyl, tolyl, benzyl or cyclohexyl; and R₉ is —OH, —COCH₃, —OCOCH₃, —SO₂NH₂, —SO₂NHCH₃, —SO₂NHC₈H₁₇, —NHSO₂CH₃,

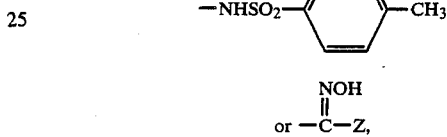

or $-\overset{\overset{NOH}{\|}}{C}-Z$, wherein Z is hydrogen, alkyl having from 1 to 10 carbon atoms, benzyl, phenethyl or phenyl.

5. A compound as defined in claim 4 wherein A is sulfur.

6. A compound as defined in claim 5 wherein R₉ is in the para position and is —OH.

* * * * *